United States Patent
Chen et al.

(10) Patent No.: US 9,290,383 B2
(45) Date of Patent: Mar. 22, 2016

(54) METHOD FOR RECYCLING EXHAUST GASES FROM FISCHER-TROPSCH SYNTHESIS

(71) Applicant: Wuhan Kaidi Engineering Technology Research Institute Co., Ltd., Wuhan (CN)

(72) Inventors: Yilong Chen, Wuhan (CN); Pingyu Kuai, Wuhan (CN); Yan Gong, Wuhan (CN); Xiaodong Zhan, Wuhan (CN); Yanfeng Zhang, Wuhan (CN); Jiaqi Jin, Wuhan (CN)

(73) Assignee: Wuhan Kaidi Engineering Technology Research Institute Co., Ltd., Wuhan (CN)

( * ) Notice: Subject to any disclaimer, the term of this patent is extended or adjusted under 35 U.S.C. 154(b) by 0 days.

(21) Appl. No.: 14/597,240

(22) Filed: Jan. 15, 2015

(65) Prior Publication Data
US 2015/0126629 A1 May 7, 2015

Related U.S. Application Data

(63) Continuation-in-part of application No. PCT/CN2013/079219, filed on Jul. 11, 2013.

(30) Foreign Application Priority Data

Jul. 17, 2012 (CN) .......................... 2012 1 0246633

(51) Int. Cl.
| | | |
|---|---|---|
| *C01B 3/16* | (2006.01) | |
| *C01B 3/34* | (2006.01) | |
| *C10K 3/04* | (2006.01) | |
| *C10G 2/00* | (2006.01) | |
| *C10K 1/00* | (2006.01) | |
| *C10K 3/06* | (2006.01) | |
| *C07C 1/04* | (2006.01) | |
| *C07C 4/06* | (2006.01) | |

(52) U.S. Cl.
CPC ... *C01B 3/16* (2013.01); *C01B 3/34* (2013.01); *C07C 1/0485* (2013.01); *C07C 4/06* (2013.01); *C10G 2/00* (2013.01); *C10G 2/30* (2013.01); *C10G 2/332* (2013.01); *C10K 1/005* (2013.01); *C10K 3/04* (2013.01); *C10K 3/06* (2013.01); *C01B 2203/0233* (2013.01); *C01B 2203/0283* (2013.01); *C01B 2203/047* (2013.01); *C01B 2203/062* (2013.01); *C01B 2203/0805* (2013.01); *C01B 2203/1241* (2013.01); *C01B 2203/142* (2013.01); *C01B 2203/84* (2013.01); *C07C 2523/755* (2013.01); *Y02P 20/121* (2015.11)

(58) Field of Classification Search
CPC ........................................................ C07B 3/16
See application file for complete search history.

(56) References Cited

U.S. PATENT DOCUMENTS 6,696,501 B2 * 2/2004 Schanke et al. ............... 518/705

FOREIGN PATENT DOCUMENTS

CN 101979468 A * 2/2011

* cited by examiner

*Primary Examiner* — Sudhakar Katakam
(74) *Attorney, Agent, or Firm* — Matthias Scholl P.C.; Matthias Scholl

(57) ABSTRACT

A method for recycling exhaust gas from Fischer-Tropsch synthesis. The method includes: 1) introducing raw gas to a shift reactor to conduct a water-gas shift reaction, and collecting shift gas; 2) introducing the shift gas to a Fischer-Tropsch synthesis device to yield a hydrocarbon fuel and exhaust gas, returning part of the exhaust gas as recycle gas; 3) introducing another part of the exhaust gas to a methanation reactor, allowing a methanation reaction to happen between the part of the exhaust gas and water vapor; 4) introducing a mixed gas product from the methanation reaction to a methane reforming reactor; 5) transporting the hydrogen and carbon monoxide resulting from the methane reforming reaction to a gas separator, separating the hydrogen and obtaining a mixed gas including carbon dioxide; and 6) returning the mixed gas including carbon dioxide to the methane reforming reactor.

11 Claims, 3 Drawing Sheets

METHOD FOR RECYCLING EXHAUST GASES FROM FISCHER-TROPSCH SYNTHESIS

CROSS-REFERENCE TO RELATED APPLICATIONS

This application is a continuation-in-part of International Patent Application No. PCT/CN2013/079219 with an international filing date of Jul. 11, 2013, designating the United States, now pending, and further claims priority benefits to Chinese Patent Application No. 201210246633.1 filed Jul. 17, 2012. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

1. Field of the Invention

The invention relates to a process for recycling exhaust gases from Fischer-Tropsch synthesis, thereby reducing carbon emissions.

2. Description of the Related Art

Typically, to improve the efficiency of the Fischer-Tropsch synthesis and to eliminate adverse effects of high CO concentration in the raw gas, incompletely reacted raw gas is returned to the inlet of the reactor to mix with fresh raw gas. However, the inert gas in the raw gas tends to accumulate in the reactor, which adversely affects the production efficiency.

The syngas from the gasification of biomass or coal often has a low hydrogen-carbon ratio, which cannot meet the requirement of the Fischer-Tropsch synthesis. In general, the raw gas is treated by water-gas shift reaction and decarbonization processes to regulate the hydrogen-carbon ratio for the Fischer-Tropsch synthesis. However, the gasification, the shift reaction, and the decarbonization are complex and require relatively high investment in the apparatus. In addition, the Fischer-Tropsch synthesis necessitates additional hydrogen for processing the product and reducing the catalyst, which increases the production costs.

SUMMARY OF THE INVENTION

In view of the above-described problems, it is one objective of the invention to provide a method for recycling exhaust gas from Fischer-Tropsch synthesis. The method can transform part of the exhaust gas into hydrogen, reduce the carbon dioxide emission, and supplies hydrogen source for the Fischer-Tropsch synthesis. The method has high production and economic efficiency.

To achieve the above objective, in accordance with one embodiment of the invention, there is provided a method for recycling exhaust gas from Fischer-Tropsch synthesis, the method comprising:

1) introducing raw gas to a shift reactor to conduct a water-gas shift reaction in the presence of a catalyst, removing carbon dioxide produced from the water-gas shift reaction, and collecting shift gas;
2) introducing the shift gas to a Fischer-Tropsch synthesis device for Fischer-Tropsch synthesis, whereby yielding a hydrocarbon fuel and exhaust gas, returning part of the exhaust gas as recycle gas and mixing the recycle gas with the shift gas, and introducing mixed gas to the Fischer-Tropsch synthesis device;
3) introducing another part of the exhaust gas to a methanation reactor, allowing a methanation reaction to happen between the part of the exhaust gas and water vapor so that hydrocarbons having two or more carbon atoms are transformed into methane;
4) introducing a mixed gas product from the methanation reaction to a methane reforming reactor, allowing a methane reforming reaction to happen between the methane and water vapor in the presence of a reforming catalyst, to yield hydrogen and carbon monoxide;
5) transporting the hydrogen and carbon monoxide resulting from the methane reforming reaction to a gas separator, separating the hydrogen and obtaining a mixed gas comprising carbon dioxide and inert components; and
6) returning the mixed gas comprising the carbon dioxide and the inert components to the methane reforming reactor as a supplementary fuel to supply heat energy.

In a class of this embodiment, in step 5), part of the separated hydrogen is introduced as a supplement to the Fischer-Tropsch synthesis device according to one of the following modes:

a. the hydrogen is first mixed with the shift gas, and then with the recycle gas, and is introduced to the Fischer-Tropsch synthesis device;
b. the hydrogen is mixed with the raw gas to yield the shift gas through the water-gas shift reaction, the shift gas is mixed with the recycle gas, and then is introduced to the Fischer-Tropsch synthesis device; and
c. the hydrogen is first mixed with the recycle gas, and then with the shift gas, and is introduced to the Fischer-Tropsch synthesis device.

In a class of this embodiment, in step 5), part of the separated hydrogen is utilized according to one or more of the following modes: d) as a material for hydrofining of Fischer-Tropsch reaction products; e) as a material for hydrocracking of Fischer-Tropsch reaction products; and f) as a reducing agent of a catalyst of Fischer-Tropsch synthesis.

In a class of this embodiment, in step 1), the raw gas is from gasification of coal or biomass and comprises hydrogen and carbon monoxide with a molar ratio thereof of between 0.1 and 2.2; the shift gas is syngas comprising more than 50% (v/v) of active components comprising hydrogen and carbon monoxide, and a molar ratio of the hydrogen and the carbon monoxide is between 1.6 and 3.0.

In a class of this embodiment, in step 1), the molar ratio of the hydrogen and the carbon monoxide in the raw gas is between 0.1 and 1.1; the shift gas comprises more than 80% (v/v) of the active components, and the molar ratio of the hydrogen and the carbon monoxide is between 2.0 and 2.5.

In a class of this embodiment, in step 1), the water-gas shift reaction is conducted at a temperature of between 200 and 500° C. under a pressure of between 0 and 4.0 MPa, through which the carbon monoxide and water vapor in the raw gas react to yield hydrogen and carbon dioxide in the presence of the catalyst.

In a class of this embodiment, in step 2), the Fischer-Tropsch synthesis is conducted at a temperature of between 160 and 350° C. under a pressure of between 0.1 and 5.0 MPa, through which the shift gas is catalyzed by a Fe- or Co-based catalyst to yield the hydrocarbon fuel.

In a class of this embodiment, in step 3), the methanation reaction is conducted at a temperature of between 250 and 450° C. under a pressure of between 0 and 4.0 MPa in the presence of a Ni-based supported catalyst, and a molar ratio of the water vapor to the part of the exhaust gas is between 0.1 and 4.

In a class of this embodiment, in step 3), the molar ratio of the water vapor to the part of the exhaust gas is between 0.5 and 1.5.

In a class of this embodiment, in step 4), the methane reforming reaction is conducted at a temperature of between 500 and 1300° C. under a pressure of between 0 and 4.0 MPa in the presence of a Ni-based, Mo-based, or Ru-based supported catalyst.

In a class of this embodiment, in step 4), water vapor is added to the mixed gas product from the methanation reaction to regulate a molar ratio of the water vapor to the mixed gas product is between 0.1 and 4.

In a class of this embodiment, in step 4), the water vapor is added to the mixed gas product from the methanation reaction to regulate the molar ratio of the water vapor to the mixed gas product is between 0.1 and 1.

Advantages according to embodiments of the invention are summarized as follows. The method can transform part of the exhaust gas into hydrogen. Conventional reforming devices requires external heat source, but the recycled hydrogen in this invention can be combusted to supply heat energy for methane reforming reactor, thereby improving the energy utilization efficiency. Specifically, the advantages include:

1. The exhaust gas of the Fischer-Tropsch synthesis comprises a large amount of alkanes, alkenes, unreacted hydrogen, and carbon monoxide; recycling the exhaust gas can significantly improve the energy utilization efficiency and economic efficiency.

2. Inert gas, for example, nitrogen, in the raw gas, tends to accumulate in the Fischer-Tropsch synthesis reactor thereby affecting the reaction efficiency. If the noncyclic exhaust gas comprising inert gas is directly transformed into syngas, it is difficult to separate inert gas from carbon monoxide, however, the separation of hydrogen of the invention can solve the problem.

3. The methane reforming reaction is an endothermic reaction; the separated hydrogen can be combusted as heat source, so there is no need to introduce external heat source, thereby saving the energy costs.

4. The large amount of hydrogen produced from the methane reforming reaction is an important source for hydrofining and hydrocracking of Fischer-Tropsch reaction products.

5. The separated hydrogen from the methane reforming reaction can be added to the raw gas which often has low hydrogen-carbon ratio, which is beneficial to decreasing the transformation depth of the raw gas and lowering the requirements for the shift reactor, thereby improving the production capacity of the Fischer-Tropsch synthesis device and reducing the production costs, and providing hydrogen source for the Fischer-Tropsch synthesis.

DETAILED DESCRIPTION OF THE EMBODIMENTS

For further illustrating the invention, experiments detailing a method for recycling exhaust gas from Fischer-Tropsch synthesis are described below. It should be noted that the following examples are intended to describe and not to limit the invention.

COMPARISON EXAMPLE

The example describes conventional Fischer-Tropsch synthesis where the produced noncyclic exhaust gas is not recycled.

1) Raw gas with low hydrogen-carbon ratio was introduced to a shift reactor at the flow rate of 5890 $NM^3/h$. The molar ratio of hydrogen to carbon monoxide in the raw gas was 0.1. A water-gas shift reaction between the hydrogen and the carbon monoxide was conducted at the temperature of 300° C. and the pressure of 2.0 MPa. After the reaction, 2350 $NM^3/h$ of carbon monoxide was transformed into carbon dioxide, together with the generation of the same volume of hydrogen. Carbon dioxide and water vapor were removed, and 4480 $NM^3/h$ of shift gas was obtained.

2) The shift gas was transported into a Fischer-Tropsch synthesis device, where 0.65 t/h of hydrocarbon fuel was produced, and 1030 $NM^3/h$ of exhaust gas was discharged.

Table 1 lists the volume percentage of components of different mixed gas

TABLE 1

| | Flow rate | Components (% v/v) | | | | | | |
|---|---|---|---|---|---|---|---|---|
| | ($NM^3/h$) | CO | $H_2$ | $CH_4$ | C2+ | $CO_2$ | $N_2$ | $H_2O$ |
| Raw gas | 5890 | 61.2 | 6.1 | 2.2 | | 23.9 | 6.5 | |
| Shift gas | 4480 | 28.1 | 60.4 | 2.9 | | | 8.6 | |
| Noncyclic exhaust gas | 1030 | 10.1 | 21.0 | 17.0 | 2.5 | 11.9 | 37.5 | |

Example 1

Figure 1:
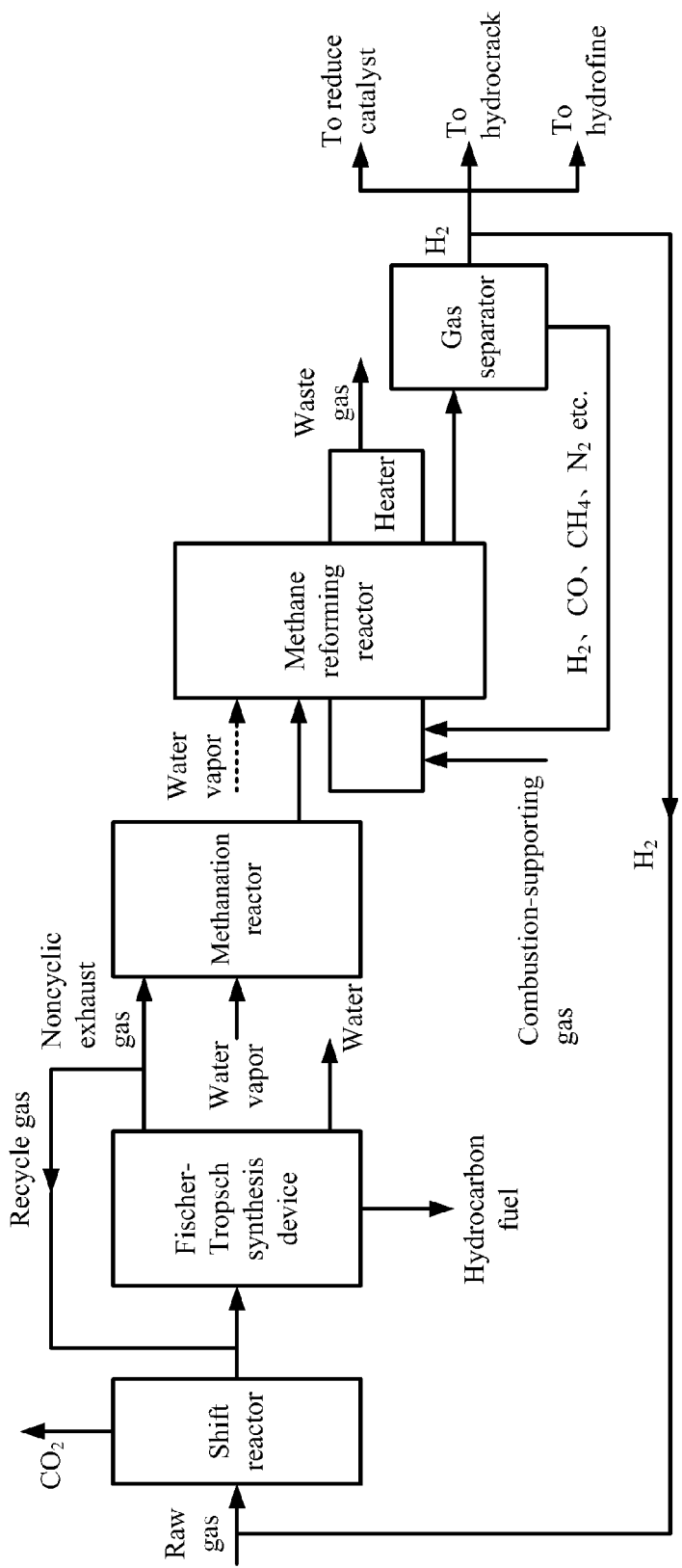
FIG. 1 is a first flow chart of a method for recycling exhaust gas from Fischer-Tropsch synthesis in accordance with one embodiment of the invention.

Raw gas involved in this example is the same as that in Comparison example, and the produced hydrogen is transported back to the shift reactor according to the flow chart in FIG. 1.

1) The raw gas was from the gasification of coal or biomass and comprised hydrogen and carbon monoxide with a molar ratio thereof of 0.1. The raw gas was introduced to a shift reactor at the flow rate of 5890 $NM^3/h$. A water-gas shift reaction between the hydrogen and the carbon monoxide was conducted at the temperature of 300° C. and the pressure of 2.0 MPa to yield hydrogen and carbon dioxide. After the reaction, 2120 $NM^3/h$ of carbon monoxide was transformed into carbon dioxide, together with the generation of the same volume of hydrogen. Carbon dioxide was removed, and 4480 $NM^3/h$ of shift gas was obtained. The molar ratio of hydrogen to carbon monoxide in the shift gas was 1.7, and the shift gas comprises more than 88% (v/v) of active components.

2) The shift gas was mixed with 715 $NM^3/h$ of hydrogen resulting from a methane reforming reactor, and transported to a Fischer-Tropsch synthesis device for Fischer-Tropsch synthesis. The Fischer-Tropsch synthesis was conducted at the temperature of 300° C. under the pressure of 2.5 MPa in the presence of a Fe-based catalyst. Thereafter, 0.75 t/h of hydrocarbon fuel was produced, and 1150 $NM^3/h$ of noncyclic exhaust gas was discharged. Part of the exhaust gas was pumped as recycle gas, which was mixed with the shift gas and then introduced to the Fischer-Tropsch synthesis device.

3) The noncyclic exhaust gas with a flow rate of 1150 NM³/h was mixed with water vapor with a flow rate of 345 NM³/h. The resulting mixed gas was cooled to 300° C. and introduced to a methanation reactor for methanation reaction. The methanation reaction was conducted at the temperature of 300° C. under the pressure of 2.0 MPa in the presence of a Ni-based supported catalyst, and the molar ratio of the water vapor to the noncyclic exhaust gas was 0.3. After the reaction, hydrocarbons having two or more carbon atoms were transformed into methane, and the mixed gas product (outlet gas) of the methanation reactor had a flow rate of 1330 NM³/h.

4) The outlet gas of the methanation reactor was transported to a subsequent dividing wall type methane reforming reactor. Water vapor was added to the mixed gas product from the methanation reaction to regulate the molar ratio of the water vapor to the mixed gas product was 2. The methane reforming reaction between the methane and water vapor was conducted at the temperature of 800° C. under the pressure of 2.0 MPa in the presence of a Ni-based supported catalyst, to yield hydrogen and carbon monoxide. The gas product from the methane reforming reactor was cooled to 45° C. and dehydrated, and had a flow rate of 1830 NM³/h.

5) The gas product from the methane reforming reactor was introduced to a pressure swing adsorption separation device, and 735 NM³/h of high purity hydrogen and 10807 NM³/h of a mixed gas comprising carbon dioxide and inert components were separated. 715 NM³/h of the high purity hydrogen was mixed with the raw gas and transformed into the shift gas through the water-gas shift reaction. The shift gas was mixed with recycle gas and then introduced to the Fischer-Tropsch synthesis device. The remaining 20 NM³/h of high purity hydrogen was utilized as a reducing agent of the catalyst of Fischer-Tropsch synthesis.

6) The mixed gas comprising carbon dioxide and inert components from the pressure swing adsorption separation device was mixed with 450 NM³/h of 93% v/v oxygen. The mixed gas was sprayed via a nozzle into a dividing wall of the methane reforming reactor and combusted to heat the methane reforming reactor.

In this example, due to the supplementation of hydrogen to the raw gas, the carbon dioxide emission from the water-gas shift reaction was decreased by 230 NM³/h, and the yield of the hydrocarbon fuel from the Fischer-Tropsch synthesis was increased from 0.65 t/h to 0.75 t/h, which was increased by 16%.

Table 2 lists the volume percentage of components of different mixed gas in Example 1.

TABLE 2

| | Flow rate | Components (% v/v) | | | | | | |
|---|---|---|---|---|---|---|---|---|
| | (NM³/h) | CO | H₂ | CH₄ | C2+ | CO₂ | N₂ | H₂O |
| Raw gas | 5890 | 61.2 | 6.1 | 2.2 | | 23.9 | 6.5 | |
| Shift gas | 4480 | 33.2 | 55.4 | 2.9 | | | 8.6 | |
| Noncyclic exhaust gas | 1150 | 10.1 | 21.0 | 17.0 | 2.5 | 11.9 | 37.5 | |
| Mixed gas product from methanation reactor | 1330 | 8.5 | 12.6 | 21.9 | | 10.2 | 31.9 | 14.9 |
| Gas product from methane reforming reactor | 1830 | 27.1 | 47.6 | 1 | | 1.3 | 23.1 | |
| Hydrogen from pressure swing adsorption separation device | 735 | | 99.9 | | | | | |
| Mixed gas from pressure swing adsorption separation device | 1080 | 45.5 | 12 | 1.7 | | 2.2 | 38.7 | |

Example 2

The treatment method of the exhaust gas in this example is the same as that in Example 1, and the produced hydrogen is transported back to the shift reactor according to the flow chart in FIG. 1.

1) The raw gas was from the gasification of coal or biomass and comprised hydrogen and carbon monoxide with a molar ratio thereof of 1.1. The raw gas was introduced to a shift reactor at the flow rate of 5950 NM³/h. A water-gas shift reaction between the hydrogen and the carbon monoxide was conducted at the temperature of 200° C. and the pressure of 1.0 MPa to yield hydrogen and carbon dioxide. After the reaction, 256 NM³/h of carbon monoxide was transformed into carbon dioxide, together with the generation of the same volume of hydrogen. Carbon dioxide was removed, and 4530 NM³/h of shift gas was obtained. The molar ratio of hydrogen to carbon monoxide in the shift gas was 1.43, and the shift gas comprises more than 88% (v/v) of active components.

2) The shift gas was mixed with 1150 NM³/h of hydrogen resulting from a methane reforming reactor, and transported to a Fischer-Tropsch synthesis device for Fischer-Tropsch synthesis. The Fischer-Tropsch synthesis was conducted at the temperature of 160° C. under the pressure of 0.1 MPa in the presence of a Co-based catalyst. Thereafter, 0.27 t/h of hydrocarbon fuel was produced, and 2420 NM³/h of noncyclic exhaust gas was discharged. Part of the exhaust gas was pumped as recycle gas, which was mixed with the shift gas and then introduced to the Fischer-Tropsch synthesis device.

3) The noncyclic exhaust gas with a flow rate of 2420 NM³/h was mixed with water vapor with a flow rate of 240 NM³/h. The resulting mixed gas was cooled to 250° C. and introduced to a methanation reactor for methanation reaction. The methanation reaction was conducted at the temperature of 250° C. under the pressure of 1.0 MPa in the presence of a Ni-based supported catalyst, and the molar ratio of the water vapor to the noncyclic exhaust gas was 0.1. After the reaction, hydrocarbons having two or more carbon atoms were transformed into methane, and the mixed gas product (outlet gas) of the methanation reactor had a flow rate of 2660 NM³/h.

4) The outlet gas of the methanation reactor was transported to a subsequent dividing wall type methane reforming reactor. Water vapor was added to the mixed gas product from the methanation reaction to regulate the molar ratio of the water vapor to the mixed gas product was 4. The methane reforming reaction between the methane and water vapor was conducted at the temperature of 500° C. under the pressure of 1.0 MPa in the presence of a Ni-based supported catalyst, to yield hydrogen and carbon monoxide. The gas product from the methane reforming reactor had a flow rate of 12400 NM$^3$/h.

5) The gas product from the methane reforming reactor was cooled to 45° C. and dehydrated, and introduced to a pressure swing adsorption separation device. 1180 NM$^3$/h of high purity hydrogen and 1780 NM$^3$/h of a mixed gas comprising carbon dioxide and inert components were separated. 540 NM$^3$/h of the high purity hydrogen was mixed with the raw gas and transformed into the shift gas through the water-gas shift reaction. The shift gas was mixed with recycle gas and then introduced to the Fischer-Tropsch synthesis device. 400 NM$^3$/h of the high purity hydrogen was utilized for hydrofining and hydrocracking of Fischer-Tropsch reaction products. The remaining 240 NM$^3$/h of high purity hydrogen was utilized as a reducing agent of the catalyst of Fischer-Tropsch synthesis.

6) The mixed gas comprising carbon dioxide and inert components from the pressure swing adsorption separation device was mixed with 950 NM$^3$/h of 93% v/v oxygen. The mixed gas was sprayed via a nozzle into a dividing wall of the methane reforming reactor and combusted to heat the methane reforming reactor.

Table 3 lists the volume percentage of components of different mixed gas in Example 2.

TABLE 3

| | Flow rate | Components (% v/v) | | | | | | |
|---|---|---|---|---|---|---|---|---|
| | (NM$^3$/h) | CO | H$_2$ | CH$_4$ | C2+ | CO$_2$ | N$_2$ | H$_2$O |
| Raw gas | 5950 | 32 | 35.4 | 2.2 | | 23.9 | 6.5 | |
| Shift gas | 4530 | 36.4 | 52.2 | 2.9 | 0.0 | 0.0 | 8.5 | |
| Noncyclic exhaust gas | 2420 | 19.5 | 37.3 | 14.7 | 1.2 | 11.4 | 15.9 | |
| Mixed gas product from methanation reactor | 2660 | 17.7 | 31.8 | 16.6 | | 10.4 | 14.5 | 0.9 |
| Gas product from methane reforming reactor | 12400 | 0.2 | 11.2 | 3.4 | | 6 | 3.1 | 76.1 |
| Hydrogen from pressure swing adsorption separation device | 1180 | | 99.9 | | | | | |
| Mixed gas from pressure swing adsorption separation device | 1780 | 1.4 | 11.7 | 23.7 | | 41.8 | 21.6 | |

In this example, due to the supplementation of hydrogen to the raw gas, the carbon dioxide emission from the water-gas shift reaction was decreased by 375 NM$^3$/h, the yield of the hydrocarbon fuel from the Fischer-Tropsch synthesis was increased from 0.21 t/h to 0.27 t/h, which was increased by 29%.

Example 3

Figure 2:
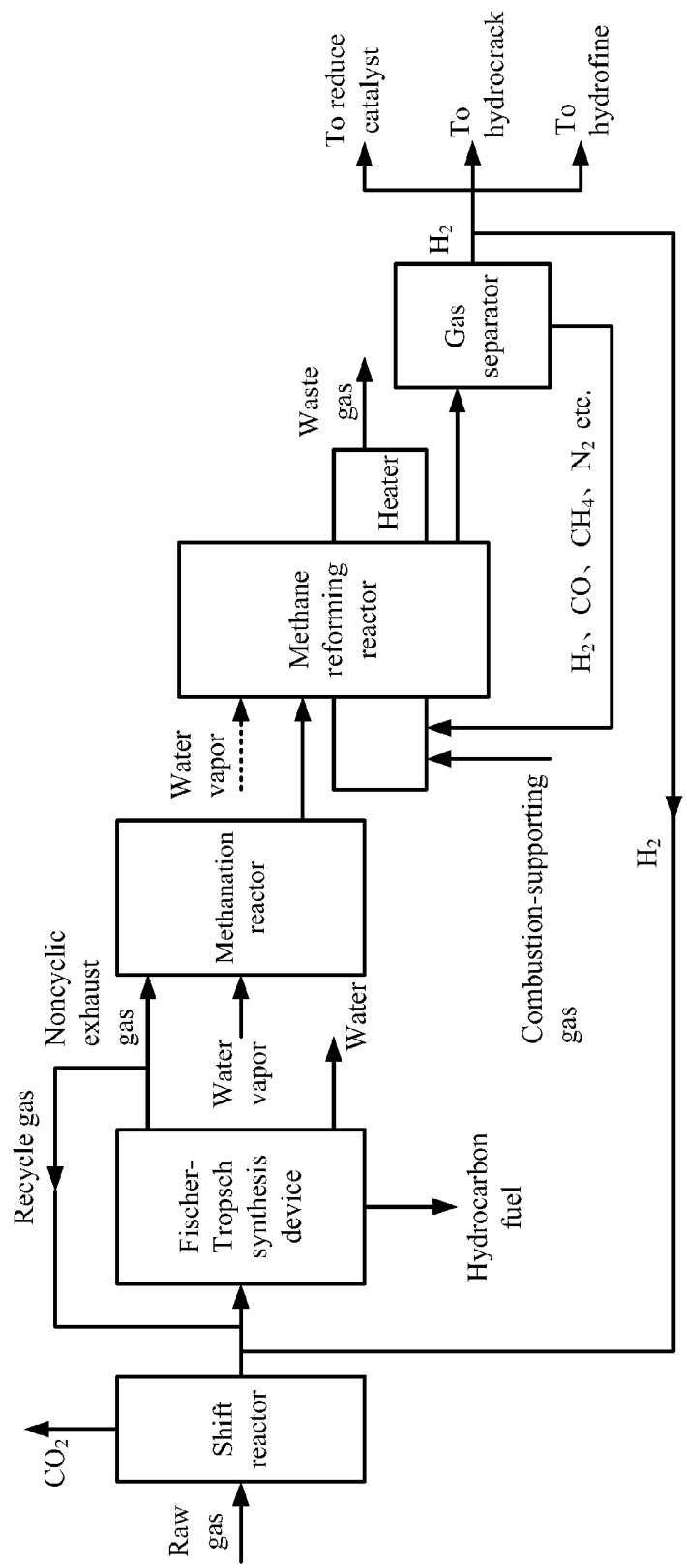
FIG. 2 is a second flow chart of a method for recycling exhaust gas from Fischer-Tropsch synthesis in accordance with one embodiment of the invention.

Raw gas involved in this example is listed in Table 4, and the produced hydrogen is transported back to the Fischer-Tropsch synthesis device according to the flow chart in FIG. 2.

1) The raw gas was from the gasification of coal or biomass and comprised hydrogen and carbon monoxide with a molar ratio thereof of 2.2. The raw gas was introduced to a shift reactor at the flow rate of 5900 NM$^3$/h. A water-gas shift reaction between the hydrogen and the carbon monoxide was conducted at the temperature of 500° C. and the pressure of 4.0 MPa to yield hydrogen and carbon dioxide. After the reaction, 300 NM$^3$/h of carbon monoxide was transformed into carbon dioxide, together with the generation of the same volume of hydrogen. Carbon dioxide was removed, and 5090 NM$^3$/h of shift gas was obtained. The molar ratio of hydrogen to carbon monoxide in the shift gas was 3.0, and the shift gas comprises more than 95% (v/v) of active components.

2) The shift gas was mixed with 100 NM$^3$/h of hydrogen resulting from a methane reforming reactor, and transported to a Fischer-Tropsch synthesis device for Fischer-Tropsch synthesis. The Fischer-Tropsch synthesis was conducted at the temperature of 350° C. under the pressure of 5 MPa in the presence of a Co-based catalyst. Thereafter, 0.72 t/h of hydrocarbon fuel was produced, and 350 NM$^3$/h of noncyclic exhaust gas was discharged. Part of the exhaust gas was pumped as recycle gas, which was mixed with the shift gas and then introduced to the Fischer-Tropsch synthesis device.

3) The noncyclic exhaust gas with a flow rate of 350 NM$^3$/h was mixed with water vapor with a flow rate of 35 NM$^3$/h. The resulting mixed gas was cooled to 450° C. and introduced to a methanation reactor for methanation reaction. The methanation reaction was conducted at the temperature of 450° C. under the pressure of 4.0 MPa in the presence of a Ni-based supported catalyst, and the molar ratio of the water vapor to the noncyclic exhaust gas was 0.1. After the reaction, hydrocarbons having two or more carbon atoms were transformed into methane, and the mixed gas product (outlet gas) of the methanation reactor had a flow rate of 384 NM$^3$/h.

4) The outlet gas of the methanation reactor was transported to a subsequent dividing wall type methane reforming reactor. Water vapor was added to the mixed gas product from the methanation reaction to regulate the molar ratio of the water vapor to the mixed gas product was 0.1. The methane reforming reaction between the methane and water vapor was conducted at the temperature of 1300° C. under the pressure of 4.0 MPa in the presence of a Ru-based supported catalyst, to yield hydrogen and carbon monoxide. The gas product from the methane reforming reactor had a flow rate of 486 NM$^3$/h.

5) The gas product from the methane reforming reactor was cooled to 45° C. and dehydrated, and introduced to a pressure swing adsorption separation device. 189 NM$^3$/h of high purity hydrogen and 297 NM$^3$/h of a mixed gas comprising carbon dioxide and inert components were separated. 124 NM$^3$/h of the high purity hydrogen was first mixed with the shift gas, and then mixed with recycle gas, and introduced to the Fischer-Tropsch synthesis device. 50 NM$^3$/h of the high purity hydrogen was utilized for hydrofining and hydrocracking of Fischer-Tropsch reaction products. The remaining 15 NM$^3$/h of high purity hydrogen was utilized as a reducing agent of the catalyst of Fischer-Tropsch synthesis.

6) The mixed gas comprising carbon dioxide and inert components from the pressure swing adsorption separation device was mixed with 150 NM$^3$/h of 93% v/v oxygen. The mixed gas was sprayed via a nozzle into a dividing wall of the methane reforming reactor and combusted to heat the methane reforming reactor.

Table 4 lists the volume percentage of components of different mixed gas in Example 3.

TABLE 4

| | Flow rate (NM³/h) | Components (% v/v) | | | | | | |
|---|---|---|---|---|---|---|---|---|
| | | CO | H₂ | CH₄ | C2+ | CO₂ | N₂ | H₂O |
| Raw gas | 5900 | 25.8 | 56.9 | 1.3 | | 13.8 | 2.2 | |
| Shift gas | 5090 | 24.0 | 71.9 | 1.5 | 0.0 | 0.0 | 2.6 | |
| Noncyclic exhaust gas | 350 | 7.2 | 24.3 | 25.8 | 1.7 | | 3.2 | 37.8 |
| Mixed gas product from methanation reactor | 384 | 6.5 | 19.0 | 28.1 | | 2.9 | 34.4 | 9.1 |
| Gas product from methane reforming reactor | 486 | 17.6 | 43.1 | 12.1 | | | 27.2 | |
| Hydrogen from pressure swing adsorption separation device | 189 | | 99.9 | | | | | |
| Mixed gas from pressure swing adsorption separation device | 297 | 28.8 | 6.9 | 19.8 | 0.0 | 0.0 | 44.5 | |

In this example, due to the supplementation of hydrogen to the raw gas, the yield of the hydrocarbon fuel from the Fischer-Tropsch synthesis was increased from 0.72 t/h to 0.73 t/h, which was increased by 2%.

Example 4

The treatment method of the exhaust gas in this example is the same as that in Example 3, and the produced hydrogen is transported back to the Fischer-Tropsch synthesis device according to the flow chart in FIG. 2.

1) The raw gas was from the gasification of coal or biomass and comprised hydrogen and carbon monoxide with a molar ratio thereof of 1. The raw gas was introduced to a shift reactor at the flow rate of 6000 NM³/h. A water-gas shift reaction between the hydrogen and the carbon monoxide was conducted at the temperature of 400° C. and the pressure of 3.0 MPa to yield hydrogen and carbon dioxide. After the reaction, 1010 NM³/h of carbon monoxide was transformed into carbon dioxide, together with the generation of the same volume of hydrogen. Carbon dioxide was removed, and 5874 NM³/h of shift gas was obtained. The molar ratio of hydrogen to carbon monoxide in the shift gas was 2.5, and the shift gas comprises more than 80% (v/v) of active components.

2) The shift gas was mixed with 1300 NM³/h of hydrogen resulting from a methane reforming reactor, and transported to a Fischer-Tropsch synthesis device for Fischer-Tropsch synthesis. The Fischer-Tropsch synthesis was conducted at the temperature of 250° C. under the pressure of 3.5 MPa in the presence of a Co-based catalyst. Thereafter, 0.69 t/h of hydrocarbon fuel was produced, and 2120 NM³/h of noncyclic exhaust gas was discharged. Part of the exhaust gas was pumped as recycle gas, which was mixed with the shift gas and then introduced to the Fischer-Tropsch synthesis device.

3) The noncyclic exhaust gas with a flow rate of 2120 NM³/h was mixed with water vapor with a flow rate of 3180 NM³/h. The resulting mixed gas was cooled to 400° C. and introduced to a methanation reactor for methanation reaction. The methanation reaction was conducted at the temperature of 400° C. under the pressure of 3.0 MPa in the presence of a Ni-based supported catalyst, and the molar ratio of the water vapor to the noncyclic exhaust gas was 1.5. After the reaction, hydrocarbons having two or more carbon atoms were transformed into methane, and the mixed gas product (outlet gas) of the methanation reactor had a flow rate of 5300 NM³/h.

4) The outlet gas of the methanation reactor was transported to a subsequent dividing wall type methane reforming reactor. Water vapor was added to the mixed gas product from the methanation reaction to regulate the molar ratio of the water vapor to the mixed gas product was 3. The methane reforming reaction between the methane and water vapor was conducted at the temperature of 900° C. under the pressure of 2.5 MPa in the presence of a Mo-based supported catalyst, to yield hydrogen and carbon monoxide. The gas product from the methane reforming reactor had a flow rate of 9005 NM³/h.

5) The gas product from the methane reforming reactor was cooled to 45° C. and dehydrated, and introduced to a pressure swing adsorption separation device. 1450 NM³/h of high purity hydrogen and 1780 NM³/h of a mixed gas comprising carbon dioxide and inert components were separated. 1050 NM³/h of the high purity hydrogen was first mixed with the shift gas, and then mixed with recycle gas, and introduced to the Fischer-Tropsch synthesis device. 325 NM³/h of the high purity hydrogen was utilized for hydrofining and hydrocracking of Fischer-Tropsch reaction products. The remaining 75 NM³/h of high purity hydrogen was utilized as a reducing agent of the catalyst of Fischer-Tropsch synthesis.

6) The mixed gas comprising carbon dioxide and inert components from the pressure swing adsorption separation device was mixed with 200 NM³/h of 93% v/v oxygen. The mixed gas was sprayed via a nozzle into a dividing wall of the methane reforming reactor and combusted to heat the methane reforming reactor.

Table 5 lists the volume percentage of components of different mixed gas in Example 4.

TABLE 5

| | Flow rate (NM³/h) | Components (% v/v) | | | | | | |
|---|---|---|---|---|---|---|---|---|
| | | CO | H₂ | CH₄ | C2+ | CO₂ | N₂ | H₂O |
| Raw gas | 6000 | 39.3 | 39.2 | 1.7 | | 2.1 | 17.7 | |
| Shift gas | 5874.0 | 22.9 | 57.3 | 1.7 | 0.0 | 0.0 | 18.1 | 0.0 |
| Noncyclic exhaust gas | 2120.0 | 9.9 | 23.4 | 11.5 | 0.3 | 4.8 | 50.1 | |
| Mixed gas product from methanation reactor | 5300 | 4.0 | 9.1 | 5.0 | | 1.9 | 20.0 | 60.0 |
| Gas product from methane reforming reactor | 9005 | 1.7 | 17.7 | | | 4.7 | 11.8 | 64.2 |
| Hydrogen from pressure swing adsorption separation device | 1450 | | 99.9 | | | | | |
| Mixed gas from pressure swing adsorption separation device | 1780 | 8.6 | 8.0 | 0.0 | 0.0 | 23.8 | 59.6 | |

In this example, due to the supplementation of hydrogen to the raw gas, the yield of the hydrocarbon fuel from the Fischer-Tropsch synthesis was increased from 0.56 t/h to 0.69 t/h, which was increased by 24%.

Example 5

Figure 3:
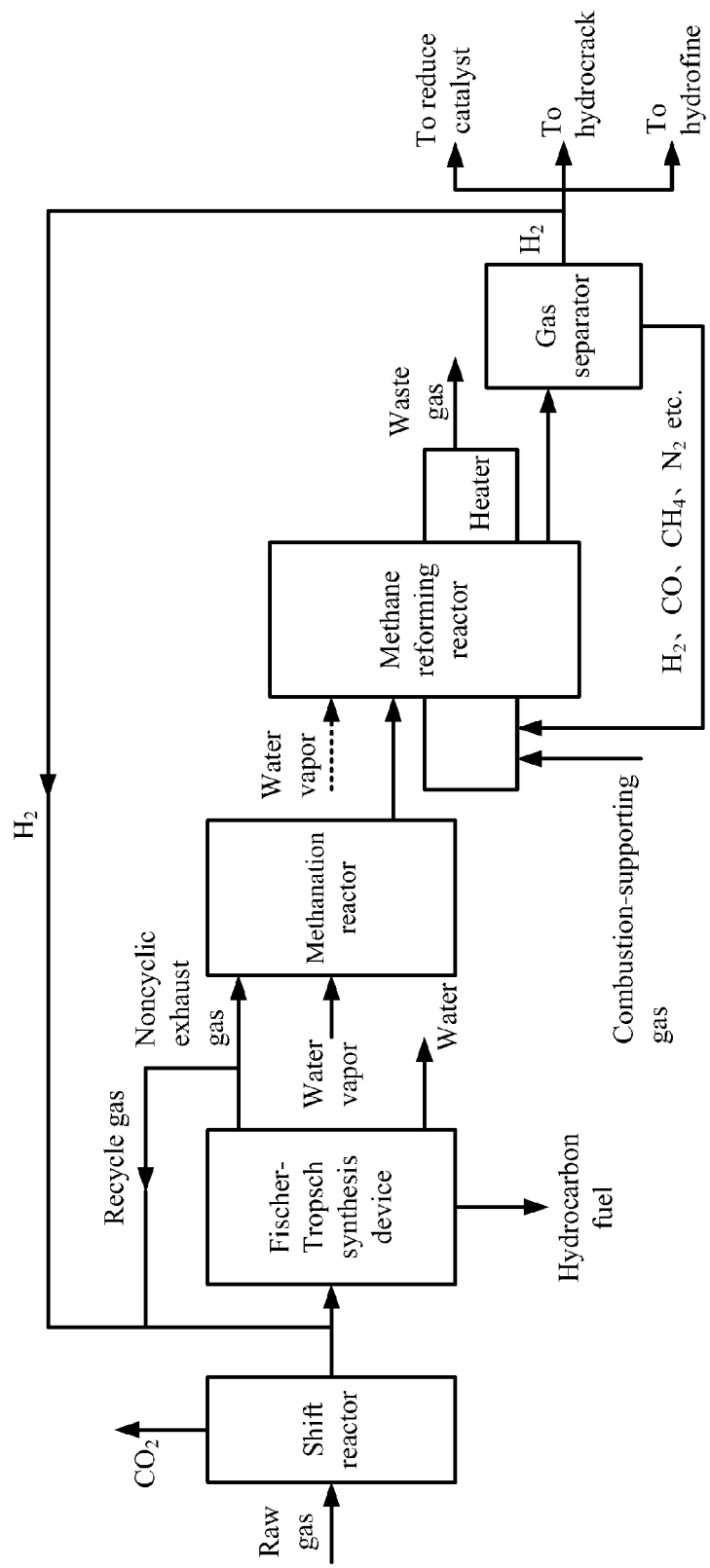
FIG. 3 is a third flow chart of a method for recycling exhaust gas from Fischer-Tropsch synthesis in accordance with one embodiment of the invention.

Raw gas involved in this example is listed in Table 6, and the produced hydrogen is first mixed with cycle gas and then transported back to the Fischer-Tropsch synthesis device according to the flow chart in FIG. 3.

1) The raw gas was from the gasification of coal or biomass and comprised hydrogen and carbon monoxide with a molar ratio thereof of 2.2. The raw gas was introduced to a shift reactor at the flow rate of 5500 NM³/h. A water-gas shift reaction between the hydrogen and the carbon monoxide was conducted at the temperature of 500° C. and the pressure of 4.0 MPa to yield hydrogen and carbon dioxide. After the reaction, 164 NM³/h of carbon monoxide was transformed into carbon dioxide, together with the generation of the same volume of hydrogen. Carbon dioxide was removed, and 4970 NM³/h of shift gas was obtained. The molar ratio of hydrogen to carbon monoxide in the shift gas was 3.0, and the shift gas comprises more than 50% (v/v) of active components.

2) The shift gas was mixed with hydrogen resulting from a methane reforming reactor with a flow rate of 715 NM³/h, and transported to a Fischer-Tropsch synthesis device for Fischer-Tropsch synthesis. The Fischer-Tropsch synthesis was conducted at the temperature of 350° C. under the pressure of 5 MPa in the presence of a Fe-based catalyst. Thereafter, 0.18 t/h of hydrocarbon fuel was produced, and 3100 NM³/h of noncyclic exhaust gas was discharged. Part of the exhaust gas was pumped as recycle gas, which was mixed with the shift gas and then introduced to the Fischer-Tropsch synthesis device.

3) The noncyclic exhaust gas with a flow rate of 3100 NM³/h was mixed with water vapor with a flow rate of 9300 NM³/h. The resulting mixed gas was cooled to 450° C. and introduced to a methanation reactor for methanation reaction. The methanation reaction was conducted at the temperature of 450° C. under the pressure of 4.0 MPa in the presence of a Ni-based supported catalyst, and the molar ratio of the water vapor to the noncyclic exhaust gas was 4. After the reaction, hydrocarbons having two or more carbon atoms were transformed into methane, and the mixed gas product (outlet gas) of the methanation reactor had a flow rate of 12400 NM³/h.

4) The outlet gas of the methanation reactor was transported to a subsequent dividing wall type methane reforming reactor. Water vapor was added to the mixed gas product from the methanation reaction to regulate the molar ratio of the water vapor to the mixed gas product was 4. The methane reforming reaction between the methane and water vapor was conducted at the temperature of 1300° C. under the pressure of 4.0 MPa in the presence of a Ni-based supported catalyst, to yield hydrogen and carbon monoxide. The gas product from the methane reforming reactor had a flow rate of 12700 NM³/h.

5) The gas product from the methane reforming reactor was cooled to 45° C. and dehydrated, and introduced to a pressure swing adsorption separation device. 630 NM³/h of high purity hydrogen and 2025 NM³/h of a mixed gas comprising carbon dioxide and inert components were separated. 440 NM³/h of the high purity hydrogen was first mixed with the cycle gas, and then mixed with the shift gas, and introduced to the Fischer-Tropsch synthesis device. 150 NM³/h of the high purity hydrogen was utilized for hydrofining and hydrocracking of Fischer-Tropsch reaction products. The remaining 40 NM³/h of high purity hydrogen was utilized as a reducing agent of the catalyst of Fischer-Tropsch synthesis.

6) The mixed gas comprising carbon dioxide and inert components from the pressure swing adsorption separation device was mixed with 150 NM³/h of 93% v/v oxygen. The mixed gas was sprayed via a nozzle into a dividing wall of the methane reforming reactor and combusted to heat the methane reforming reactor.

Table 6 lists the volume percentage of components of different mixed gas in Example 5.

TABLE 6

| | Flow rate (NM³/h) | Components (% v/v) | | | | | | |
|---|---|---|---|---|---|---|---|---|
| | | CO | $H_2$ | $CH_4$ | C2+ | $CO_2$ | $N_2$ | $H_2O$ |
| Raw gas | 5500 | 14.7 | 32.2 | 0.3 | | 9.7 | 43.1 | |
| Shift gas | 4966.5 | 13.0 | 39.0 | 0.3 | 0.0 | 0.0 | 47.7 | |
| Noncyclic exhaust gas | 3100.0 | 4.1 | 11.3 | 4.1 | 0.3 | 3.8 | 76.4 | |
| Mixed gas product from methanation reactor | 12400 | 1.0 | 2.8 | 1.0 | | 1.0 | 19.1 | 75.0 |
| Gas product from methane reforming reactor | 12700 | 0.8 | 7.7 | | | 2.4 | 18.6 | 70.5 |
| Hydrogen from pressure swing adsorption separation device | 630 | | 99.9 | | | | | |
| Mixed gas from pressure swing adsorption separation device | 2025 | 3.6 | 3.1 | 0.0 | 0.0 | 10.7 | 82.7 | |

In this example, due to the supplementation of hydrogen to the raw gas, the yield of the hydrocarbon fuel from the Fischer-Tropsch synthesis was increased from 0.16 t/h to 0.18 t/h, which was increased by 13%.

The working principle and working process of the invention are summarized as follows. The raw gas is transformed in the shift reactor and then introduced to a Fischer-Tropsch synthesis device for reaction to yield hydrocarbon fuel and exhaust gas. Part of the exhaust gas is used as recycle gas and transported back to the outlet of the Fischer-Tropsch synthesis device. The other part of the exhaust gas is mixed and reacts with water vapor in a methanation reactor. The produced mixed gas is introduced to a methane reforming reactor where methane and water vapor react to produce a first mixed gas comprising carbon monoxide and hydrogen. The first mixed gas comprising carbon monoxide and hydrogen is introduced to a separation device and thus high purity hydrogen and a second mixed gas comprising carbon monoxide. The second mixed gas comprising carbon monoxide is combusted to supply heat energy for the methane reforming reactor. The high purity hydrogen can be utilized for the deep processing or deacidification of Fischer-Tropsch synthesis products, and part of the hydrogen is mixed with the raw gas to participate in the Fischer-Tropsch synthesis. The method employs syngas as the raw gas in the Fischer-Tropsch synthesis and recycles the exhaust gas, specifically, to separate hydrogen from the exhaust gas, thereby reducing the carbon dioxide emission and providing new hydrogen source for the Fischer-Tropsch synthesis, with high production and economic efficiency. The invention involves a Fischer-Tropsch synthesis and methane reforming device, which can transform light hydrocarbon-rich exhaust gas into hydrogen which is separated and purified for the Fischer-Tropsch synthesis.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for recycling exhaust gas from Fischer-Tropsch synthesis, the method comprising:
   1) introducing raw gas obtained from gasification of coal or biomass to a shift reactor, the raw gas comprising hydrogen and carbon monoxide, conducting a water-gas shift reaction in the presence of a catalyst and, in the presence of water vapor, transforming a part of the carbon monoxide in the raw gas to carbon dioxide and hydrogen, removing carbon dioxide produced from the water-gas shift reaction, and collecting syngas; wherein: a molar ratio of hydrogen to carbon monoxide in the raw gas is between 0.1 and 2.2; the syngas comprises more than 50% (v/v) of hydrogen and carbon monoxide, and a molar ratio of hydrogen to carbon monoxide in the syngas is between 1.6 and 3.0;
   2) introducing the syngas to a Fischer-Tropsch reactor for Fischer-Tropsch synthesis, whereby yielding a hydrocarbon fuel and exhaust gas, returning part of the exhaust gas as recycle gas and mixing the recycle gas with the syngas to obtain a first gas mixture, and introducing the first gas mixture to the Fischer-Tropsch reactor;
   3) introducing the remainder of the exhaust gas to a methanation reactor, allowing hydrocarbons having two or more carbon atoms in remainder of the exhaust gas and water vapor to react via a methanation reaction to produce methane, and obtaining a second gas mixture comprising methane;
   4) introducing the second gas mixture to a methane reforming reactor, allowing methane in the second gas mixture and water vapor to react via a methane reforming reaction in the presence of a reforming catalyst, to yield hydrogen and carbon monoxide, and obtaining a third gas mixture comprising hydrogen and carbon monoxide;
   5) transporting the third gas mixture from the methane reforming reactor to a gas separator, separating hydrogen from the third gas mixture, and obtaining a fourth gas mixture comprising carbon monoxide and inert components;
   6) introducing a first part of the hydrogen obtained in step 5) to the Fischer-Tropsch reactor; and
   7) returning the fourth gas mixture comprising carbon monoxide and the inert components to the methane reforming reactor as a supplementary fuel to supply to supply heat energy.

2. The method of claim 1, wherein in step 6), the first part of the hydrogen is introduced to the Fischer-Tropsch reactor according to one of the following modes:

a) the first part of the hydrogen is first mixed with the syngas, and then with the recycle gas, and is introduced to the Fischer-Tropsch reactor;
   b) the first part of the hydrogen is mixed with the raw gas to yield the syngas through the water-gas shift reaction, the syngas is mixed with the recycle gas, and then is introduced to the Fischer-Tropsch reactor; and
   c) the first part of the hydrogen is first mixed with the recycle gas, and then with the syngas, and is introduced to the Fischer-Tropsch reactor.

3. The method of claim 2, wherein a second part of the hydrogen obtained in step 5) is utilized according to one or more of the following modes:

a) as a material for hydrofining of Fischer-Tropsch reaction products;
   b) as a material for hydrocracking of Fischer-Tropsch reaction products; and
   c) as a reducing agent of a catalyst of Fischer-Tropsch synthesis.

4. The method of claim 1, wherein in step 1), the molar ratio of hydrogen to carbon monoxide in the raw gas is between 0.1 and 1.1; the syngas comprises more than 80% (v/v) of hydrogen to carbon monoxide, and the molar ratio of hydrogen to carbon monoxide is between 2.0 and 2.5.

5. The method of claim 2, wherein in step 1), the water-gas shift reaction is conducted at a temperature of between 200 and 500° C. under a pressure of between 0 and 4.0 MPa.

6. The method of claim 2, wherein in step 2), the Fischer-Tropsch synthesis is conducted at a temperature of between 160 and 350° C. under a pressure of between 0.1 and 5.0 MPa, and in the presence of a Fe- or Co-based catalyst.

7. The method of claim 2, wherein in step 3), the methanation reaction is conducted at a temperature of between 250 and 450° C. under a pressure of between 0 and 4.0 MPa in the presence of a Ni-based supported catalyst, and a molar ratio of the water vapor to the remainder of the exhaust gas is between 0.1 and 4.

8. The method of claim 7, wherein in step 3), the molar ratio of the water vapor to the remainder of the exhaust gas is between 0.5 and 1.5.

9. The method of claim 2, wherein in step 4), the methane reforming reaction is conducted at a temperature of between 500 and 1300° C. under a pressure of between 0 and 4.0 MPa in the presence of a Ni-based, Mo-based, or Ru-based supported catalyst.

10. The method of claim 9, wherein in step 4), water vapor is added to the second gas mixture to regulate a molar ratio of the water vapor to the second gas mixture to be between 0.1 and 4.

11. The method of claim 10, wherein in step 4), the water vapor is added to the second gas mixture to regulate the molar ratio of the water vapor to the second gas mixture to be between 0.1 and 1.

* * * * *